United States Patent [19]

Whittaker

[11] 4,259,496

[45] Mar. 31, 1981

[54] HALOGENATION OF PYRIDINE COMPOUNDS

[75] Inventor: Graham Whittaker, Runcorn, England

[73] Assignee: Imperial Chemical Industries Limited, London, England

[21] Appl. No.: 112,609

[22] Filed: Jan. 16, 1980

[30] Foreign Application Priority Data

Jan. 29, 1979 [GB] United Kingdom ............... 03018/79

[51] Int. Cl.³ ........................................... C07D 213/26
[52] U.S. Cl. .................................... 546/345; 546/346
[58] Field of Search ......................................... 546/345

[56] References Cited

U.S. PATENT DOCUMENTS

| 4,031,100 | 6/1977 | Giacobbe | 546/345 |
| 4,071,521 | 1/1978 | Muench | 546/345 |
| 4,101,554 | 7/1978 | Tobin | 546/345 |

*Primary Examiner*—Alan L. Rotman
*Attorney, Agent, or Firm*—Cushman, Darby & Cushman

[57] ABSTRACT

Side-chain fluorination of 3-methylpyridine is carried out by reaction with hydrogen fluoride and chlorine in the liquid phase. The main products are 3-trifluoromethylpyridine, 3-chlorodifluoropyridine and 3-difluoromethylpyridine.

2 Claims, No Drawings

HALOGENATION OF PYRIDINE COMPOUNDS

This invention relates to the halogenation of pyridine compounds, and more particularly to a process for the side-chain fluorination or chlorofluorination of 3-methylpyridine.

3-trifluoromethylpyridine and 3-perchlorofluoromethylpyridines are useful intermediates in the preparation of compounds having herbicidal activity. Thus, for example, 3-trifluoromethylpyridine and 3-chlorodifluoromethylpyridine may be chlorinated to yield respectively 2-chloro-5-trifluoromethylpyridine and 2-chloro-5-chlorodifluoromethylpyridine, which may in turn be used as intermediates in the preparation of herbicides, as described for example in the specification of UK Application GB No. 2002 368 A.

According to the present invention there is provided a process for the preparation of 3-trifluoromethylpyridine, a 3-perchlorofluoromethylpyridine, or 3-difluoromethylpyridine (or a derivative thereof containing one or more chlorine or fluorine atoms as substituent(s) in the pyridine ring) characterised in that 3-methylpyridine is reacted with hydrogen fluoride and chlorine in the liquid phase at elevated temperature and superatmospheric pressure, the proportion of hydrogen fluoride employed being at least 3 moles per mole of 3-methylpyridine.

The proportion of chlorine employed is preferably at least 3 moles of chlorine (for example from 3 to 10 moles) per mole of 3-methylpyridine.

The proportion of hydrogen fluoride is preferably at least 5 moles of HF per mole of 3-methylpyridine, for example from 5 to 50 moles of HF per mole of 3-methylpyridine; higher proportions of HF may be used if desired and indeed a large excess of HF may be used as reaction medium.

The reaction is preferably carried out under substantially anhydrous conditions. The reaction may conveniently be carried out, for example, by dissolving the 3-methylpyridine in substantially anhydrous liquid hydrogen fluoride in a pressure vessel, introducing gaseous chlorine until the desired pressure is attained and then heating the reaction mixture.

The reaction is preferably carried out at a temperature in the range from 50° C. to 300° C.; the range from 100° C. to 250° C. is especially preferred.

The reaction is preferably carried out at a gauge pressure of at least 2 bar (for example from 2 to 30 bar). The reaction period required will depend upon the temperature and pressure employed but in general a reaction period of at least 1 hour is preferred, for example from 2 hours to 20 hours.

A small proportion of a free-radical initiator (for example bromine or a peroxide such as dibenzoyl peroxide) may be added if desired; this is not essential but in some instances may enable the reaction to be carried out at a somewhat lower temperature than would be required in the absence of such an initiator.

The main products of the reaction are, in general, 3-trifluoromethylpyridine, 3-chlorodifluoromethylpyridine and 3-difluoromethylpyridine, the relative proportions depending upon such factors as the excess of hydrogen fluoride and chlorine employed, the reaction temperature and the period of reaction.

A proportion of 2-chloro-5-trifluoromethylpyridine or 2-chloro-5-chlorodifluoromethylpyridine, or other derivatives containing one or more chlorine or fluorine atoms as substituents in the pyridine ring, may also be obtained. Any 3-difluoromethylpyridines produced may, if desired, be converted into 3-trifluoromethylpyridine or 3-chlorotrifluoromethylpyridine, either by recycling to the process or by separate conversion.

The fluorinated or chlorofluorinated products of the reaction may be separated by conventional techniques, for example solvent extraction, fractional distillation and fractional crystallisation.

The invention is illustrated by the following Examples.

EXAMPLE 1

3-methylpyridine (180 g, 1.94 mole) was mixed with anhydrous HF (10 mole) in an "Inconel" stirred autoclave fitted with a reflux condenser and automatic pressure control valve. The heat of mixing caused the temperature of the reaction mixture to rise to 90° C.; chlorine gas was then introduced into the mixture at a rate of 3.9 g min$^{-1}$ with vigorous stirring. The maximum pressure was restricted to 440 psi by venting off HCl and excess chlorine through the pressure control valve into a scrubber. The temperature of the reaction mixture was gradually raised from 90° C. to 190° C. over 4.5 hours and maintained at this temperature for a further 1.5 hours. The total quantity of chlorine introduced was 1.4 kg (19.8 moles). A further 400 g (20 moles) of HF were then added to the reaction mixture and the whole heated to 200° C. for 12 hours at 200 psi.

The cooled crude product was quenched with water and excess HF was neutralised with 40% KOH. Steam distillation yielded 130 g of a colourless organic liquid. Analysis by nuclear magnetic resonance ($^{19}$F) and gas chromatography showed this to be predominantly 3-trifluoromethylpyridine (74.2% by weight), together with 3-difluorochloromethylpyridine (13.1% by weight) and 3-difluoromethylpyridine (12.7% by weight). Distillation of the mixture yielded 3-trifluoromethylpyridine bp 114° C. (overall yield 34%) together with a fraction of 3-difluorochloromethylpyridine and 3-difluoromethylpyridine (overall yield 12%) suitable for recycling.

EXAMPLE 2

3-methylpyridine (180 g, 1.94 mole) and anhydrous HF (450 g, 22.5 moles) were mixed in the apparatus described in Example 1. The mixture was heated to 120° C. and chlorine gas was passed, with stirring, through the mixture at 3.9 g min$^{-1}$ for 6 hours, the temperature being raised from 120° C. to 190° C. over 4 hours and then maintained at 190° C. for 2 hours. Total chlorine introduced was 1.4 kg (19.8 moles). At the end of this period a further 150 g of HF (7.5 moles) were pumped into the autoclave. The mixture was then heated to 200° C. for 6 hours at 230 psi.

The cooled reaction product was quenched with water, neutralised with 40% KOH and steam-distilled to yield 142.5 g of colourless organic product. Analysis of this product (as in Example 1) showed it to be mainly 3-difluorochloromethylpyridine (76.5%) together with 3-difluoromethylpyridine (21.7%) and 3-trifluoromethylpyridine (1.8%). These compounds were separated by distillation.

EXAMPLE 3

3-methylpyridine (0.36 mole) was mixed with anhydrous liquid hydrogen fluoride (5 moles) in a pressure vessel and liquid bromine (0.04 mole) was added. Gaseous chlorine was introduced until the gauge pressure was 3 bar and the temperature was then raised to 240° C. After 3 hours at this temperature, the mixture was cooled, the gases were vented and the contents of the vessel were repressurised to 3 bar with chlorine. The mixture was again heated to 240° C. for 3 hours, followed by cooling and venting. This sequence was repeated a further 4 times. After the final cooling, the reaction mixture was poured onto ice and neutralised with sodium bicarbonate. The organic products were extracted with methylene chloride and analysis (nuclear magnetic resonance, confirmed by mass spectra) showed that the product contained 3-trifluoromethylpyridine, 3-difluoromethylpyridine and 2-chloro-5-trifluoromethylpyridine.

EXAMPLE 4

3-methylpyridine (0.26) mole was mixed with anhydrous liquid hydrogen fluoride (5 moles) in a pressure vessel and dibenzoyl peroxide (0.01 mole) was added. Gaseous chlorine was introduced until the gauge pressure was 3 bar and the temperature was then raised to 95° C. After 2 hours at this temperature the mixture was cooled, the gases were vented and the contents of the vessel were repressurised to 3 bar with chlorine. The mixture was then heated to 200° C. for 4 hours. At the end of this period the mixture was cooled, neutralised and extracted with methylene chloride. The product was found by analysis (as before) to contain 3-trifluoromethylpyridine.

I claim:

1. A process for the preparation of a fluorinated pyridine derivative from the group consisting of 3-trifluoromethylpyridine, 3-perchlorofluoromethylpyridines, 3-difluoromethylpyridine and derivatives thereof containing one or more chlorine or fluorine atoms as substituent(s) in the pyridine ring comprising reacting 3-methylpyridine with hydrogen fluoride and chlorine in the liquid phase at an elevated temperature in the range of 50° C. to 300° C. and superatmospheric pressure in the presence of chlorine, the proportion of hydrogen fluoride employed being at least 3 moles per mole of 3-methylpyridine and the proportion of chlorine being at least 3 moles per mole of 3-methylpyridine.

2. A process according to claim 1 wherein the proportion of hydrogen fluoride is from 5 to 50 moles of HF per mole of 3-methylpyridine.

* * * * *